United States Patent
Narula et al.

(10) Patent No.: US 6,756,507 B2
(45) Date of Patent: Jun. 29, 2004

(54) PROCESS FOR THE PREPARATION OF SODIUM SALTS OF STATINS

(75) Inventors: Pardeep Narula, Delhi (IN); Srinivasan Raman, Tamil Nadu (IN); M. Lakshmi Kumar, Andhra Pradesh (IN); Parveen Kumar, Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 93 days.

(21) Appl. No.: 10/149,625

(22) PCT Filed: Dec. 14, 2000

(86) PCT No.: PCT/IB00/01873

§ 371 (c)(1),
(2), (4) Date: Sep. 4, 2002

(87) PCT Pub. No.: WO01/44144

PCT Pub. Date: Jun. 21, 2001

(65) Prior Publication Data

US 2003/0050502 A1 Mar. 13, 2003

(30) Foreign Application Priority Data

Dec. 17, 1999 (IN) ........................................ 1546/DEL/99

(51) Int. Cl.$^7$ ............................................... C07C 69/28
(52) U.S. Cl. ..................................... 560/256; 560/119
(58) Field of Search ................................ 560/256, 119

(56) References Cited

U.S. PATENT DOCUMENTS

| | | | |
|---|---|---|---|
| 4,346,227 A | 8/1982 | Terahara et al. | |
| 4,432,996 A | 2/1984 | Gullo et al. | |
| 4,447,626 A | 5/1984 | Terahara et al. | |
| 4,448,979 A | 5/1984 | Terahara et al. | |
| 5,559,241 A | 9/1996 | Corsi et al. | |

FOREIGN PATENT DOCUMENTS

WO    WO 98/56750    12/1998

*Primary Examiner*—Paul J. Killos
(74) *Attorney, Agent, or Firm*—Jayadeep R. Deshmukh

(57) ABSTRACT

A process for the preparation of sodium salts of statins, namely Compactin, Lovastatin and Pravastatin.

13 Claims, No Drawings

PROCESS FOR THE PREPARATION OF SODIUM SALTS OF STATINS

This application is a 371 of PCT/IB00/01873 filed Dec. 14, 2000.

FIELD OF THE INVENTION

The present invention relates to a process for the preparation of sodium salts of statins, namely Compactin, Lovastatin and Pravastatin having the Formula Ia:

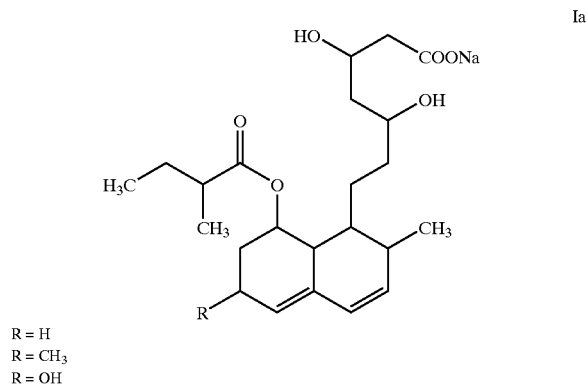

R = H
R = CH₃
R = OH

BACKGROUND OF THE INVENTION

The "statins" are a family of compounds that are usually inhibitors of 3-hydroxy-3-methylglutaryl coenzyme A (HMG-CoA) reductase, the rate-limiting enzyme in cholesterol biosynthesis. As HMG-CoA reductase inhibitors, the statins are able to reduce plasma cholesterol levels in various mammalian species, including humans and are therefore effective in the treatment of hypercholesterolaemia.

Of all the statins known only two are produced directly by fermentation. These are Lovastatin (also called mevinolin or monacolin-K) and Compactin (also called mevastatin or ML-236B). Other statins are produced either chemically or enzymatically derived from Lovastatin or Compactin. One of these is Pravastatin, which has found favour recently as a more potent HMG-CoA reductase inhibitor than Lovastatin or Compactin and is disclosed in U.S. Pat. No. 4,346,227.

Preparation of sodium salts of these compounds has been described in U.S. Pat. Nos. 4,448,979; 4,346,227; and 4,447,626. The methods employ use of alkali, acid, solvents, ion exchange chromatography followed by freeze drying operation using either the lactone or methyl ester form of Pravastatin as the raw material.

Further, U.S. Pat. No. 4,432,996 describes a method for the preparation of sodium salts of compactin. This method employs compactin lactone form as the starting material and involves sodium salt formation using sodium hydroxide and its subsequent isolation by taking to dryness 'in vacuo'.

The isolation method reported till now comprises complete removal of the solvent by either freeze drying or dryness under vacuum. In addition, the process involves an elaborate extraction procedure for the work up and is uneconomical at commercial manufacturing scale because of large number of steps. This operation is time consuming and also involves capital intensive equipment at industrial scale.

The recent commercial introduction of chemically synthesized HMG-CoA reductase inhibitors has provided a need for development of high yielding processes for production of fermentation-based statins. The techniques to improve the processes include, but are not limited to, improving the producer microorganisms, scale up of the process, improving the culture medium or simplifying downstream recovery process.

DESCRIPTION OF THE INVENTION

It is an object of the present invention to solve the problems associated with the prior art and to provide a simplified and efficient method for the preparation of sodium salts of these statins using conditions which are convenient to operate on commercial scale.

The present invention specifically describes a process for the preparation and isolation of sodium salts of statins of Formula Ia. The process comprises contacting a solution of the hydroxy acid form of the statins of Formula Ib

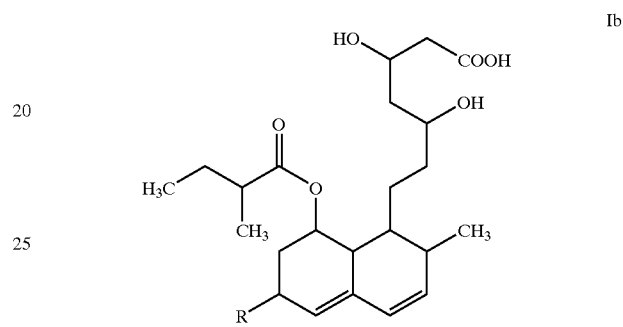

with sodium 2-ethylhexanoate and recovering the corresponding sodium salts of the statins from a solution thereof.

According to the present invention, the starting material is hydroxy acid form of the statins or is generated in situ from the lactone form or other ester or salts of the statins. Sodium 2-ethylhexanoate is prepared by the methods known in the literature.

Solvents which may be used are generally selected depending upon the solubility of the hydroxy acid form of the statins and preferably are water-immiscible organic solvents. These include chlorinated hydrocarbons such as chloroform, dichloromethane, dichloroethane etc., aromatic hydrocarbons, such as benzene, toluene, xylene, ketones such as methyl ethyl ketone, methyl isobutyl ketone or esters such as ethyl acetate, butyl acetate, isopropyl acetate or isobutyl acetate or mixtures thereof. The preferred solvent being ethyl acetate from economics point of view.

Methods known in the art may be used with the process of this invention to enhance any aspect of this process. For example, slurry may be cooled prior to filtration or a miscible "anti-solvent" can be advantageously used to complete crystallization. Preferably, the anti-solvent is selected from a group of solvents, like acetone and acetonitrile, most preferred being acetone or water immiscible solvents like ether and hexane.

The following examples illustrate the present invention and are not intended to be limiting the scope of the invention.

EXAMPLE 1

Preparation of Sodium Salt of Pravastatin (Ia, R=OH)

5 g of lactone form of Pravastatin, isolated as a crude product from the fermentation broth of a species of Streptomyces, is suspended in 15 ml of methanol:water (1:2) mixture containing about 3% w/v sodium hydroxide. The reaction mixture is warmed to 35° C. and stirred for 40–60 minutes until the hydrolysis is complete. The pH of the solution is adjusted to ~4.0 using concentrated hydrochloric acid. The hydroxy acid form of Pravastatin is extracted in ethyl acetate by stirring for 20–30 minutes and dried over anhydrous sodium sulfate. Stoichiometric quantity of sodium 2-ethyl hexanoate is added to the ethyl acetate layer and stirred gently at room temperature for 2 hours until the precipitate of sodium salt of Pravastatin appears. The slurry is cooled to 5–10° C., further stirred for 60 minutes and the product is filtered, washed and dried to afford about 2.8 g of Pravastatin sodium salt as a dry powder.

EXAMPLE 2

When the process is carried out as described in Example 1 up to the stage where the precipitate of sodium salt of Pravastatin appears, 12.5 ml of acetone is added to the slurry, cooled to 5–10° C. and stirred for 60 minutes. The product is isolated by filtration and about 3.2 g of Pravastatin sodium salt is obtained as a dry powder.

EXAMPLE 3
Preparation of Sodium Salt of Compactin (Ia, R=H)

5 g of lactone form of Compactin, isolated in crude form from the fermentation broth of a species of Penicillium, is suspended in 15 ml of methanol:water (1:2) mixture containing about 3% sodium hydroxide. The reaction mixture is warmed to 35° C. and stirred until the hydrolysis is completed. The pH of the solution is adjusted to ~4.0 using concentrated hydrochloric acid. The hydroxy acid of Compactin is extracted in ethyl acetate and dried over anhydrous sodium sulfate. Stoichiometric quantity of sodium 2-ethyl hexanoate is added to ethyl acetate and stirred gently until the precipitate of sodium salt of Compactin appears. The slurry is cooled to 5–10° C. and stirred for 60 minutes. About 2.5 g of Compactin sodium salt is isolated as a dry powder.

EXAMPLE 4

When the process is carried out as detailed above up to the stage where the precipitate of sodium salt of Compactin appears, 12.5 ml of acetone is added to the slurry and cooled to 5–10° C., stirred for 60 minutes and about 2.9 g of Compactin sodium salt is isolated as a dry powder.

EXAMPLE 5
Preparation of Sodium Salt of Lovastatin (Ia, R=CH$_3$)

5 g of lactone form of Lovastatin isolated from the fermentation broth of a species of Aspergillus is suspended in 15 ml of methanol:water (1:2) mixture containing about 3% sodium hydroxide. The reaction mixture is warmed to 35° C. and stirred until the hydrolysis is complete. The pH of the solution is adjusted to ~4.0 using concentrated hydrochloric acid. The hydroxy acid of Lovastatin is extracted in ethyl acetate and dried over anhydrous sodium sulfate. Stoichiometric quantity of sodium 2-ethyl hexanoate is added to the ethyl acetate and stirred gently until the precipitate of sodium salt of Lovastatin appears. 12.5 ml of acetone is added to the slurry. The slurry is cooled to 5–10° C. and stirred for 60 minutes. About 4.0 g of Lovastatin sodium salt is isolated as a dry powder.

While the present invention has been described in terms of its specific embodiments, certain modifications and equivalents will be apparent to those skilled in the art and are intended to be included within the scope of the present invention.

We claim:

1. A process for the preparation of sodium salts of the statins of following formula:

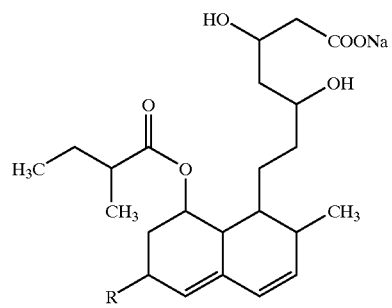

wherein R=H, CH$_3$, or OH, which comprises contacting a solution of hydroxy acid form of the statins having the formula:

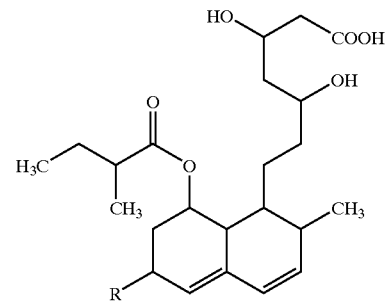

with sodium 2-ethylhexanoate and recovering the corresponding sodium salts of the statins from a solution thereof.

2. A process of claim 1 wherein the starting material is in hydroxy acid form or is generated in situ from the lactone form or other ester or salts of the statins.

3. A process as claimed in 1, wherein said solution consists of a solvent or a mixture of solvents chosen from chlorinated hydrocarbons, aromatic hydrocarbons, ketones, esters and mixtures thereof.

4. A process as claimed in claim 3, wherein the chlorinated hydrocarbons is selected from chloroform, dichloromethane or dichloroethane.

5. A process as claimed in claim 3 wherein said ketone is methyl isobutyl ketone or methyl ethyl ketone.

6. A process as claimed in claim 3 wherein the aromatic hydrocarbons is selected from toluene, xylene or benzene.

7. A process as claimed in 3 wherein said ester is selected from ethyl acetate, butyl acetate, isopropyl acetate or isobutyl acetate.

8. A process as claimed in claim 7 wherein said solvent is ethyl acetate.

9. A process as claimed in claim 3 wherein a miscible anti-solvent is added to enhance the precipitation.

10. A process as claimed in claim 9, wherein the anti-solvent is an organic solvent like acetone, acetonitrile, ether or hexane.

11. A process as claimed in claim 10 wherein said anti-solvent is acetone.

12. The process of claim 1 wherein the sodium salts of the statins are recovered by filtration.

13. The process of claim 12 wherein the slurry is cooled prior to filtration.

* * * * *